(12) United States Patent
Habuchi et al.

(10) Patent No.: US 10,711,094 B2
(45) Date of Patent: Jul. 14, 2020

(54) CONJUGATED POLYMER NANOPARTICLES, METHODS OF USING, AND METHODS OF MAKING

(71) Applicant: KING ABDULLAH UNIVERSITY OF SCIENCE AND TECHNOLOGY, Thuwal (SA)

(72) Inventors: Satoshi Habuchi, Thuwal (SA); Hubert Marek Piwonski, Thuwal (SA); Tsuyoshi Michinobu, Tokyo (JP)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 39 days.

(21) Appl. No.: 15/748,247

(22) PCT Filed: Sep. 7, 2016

(86) PCT No.: PCT/IB2016/055330
§ 371 (c)(1),
(2) Date: Jan. 29, 2018

(87) PCT Pub. No.: WO2017/042695
PCT Pub. Date: Mar. 16, 2017

(65) Prior Publication Data
US 2018/0223036 A1    Aug. 9, 2018

Related U.S. Application Data

(60) Provisional application No. 62/216,584, filed on Sep. 10, 2015.

(51) Int. Cl.
*B32B 5/16* (2006.01)
*C08G 61/12* (2006.01)
(Continued)

(52) U.S. Cl.
CPC ........ *C08G 61/126* (2013.01); *A61K 49/0019* (2013.01); *A61K 49/0021* (2013.01); *C07D 417/14* (2013.01); *C08G 61/123* (2013.01); *C08G 61/124* (2013.01); *C08J 3/07* (2013.01); *C08J 3/12* (2013.01); *C09K 11/06* (2013.01); *G01N 33/582* (2013.01);
(Continued)

(58) Field of Classification Search
CPC ............................. H01L 51/0035; C08G 63/81
See application file for complete search history.

(56) References Cited

U.S. PATENT DOCUMENTS

2014/0328764 A1    11/2014   Tang et al.
2015/0249214 A1*   9/2015    Watanabe ............... H01L 51/42
                                                              136/263

FOREIGN PATENT DOCUMENTS

WO    2014017983 A1    1/2014
WO    2015017586 A1    2/2015

OTHER PUBLICATIONS

Pecher & Mecking, Nanoparticles of Conjugated Polymers, Chem. Rev. 2010, 110, 6260-6279 (Year: 2010).*

(Continued)

*Primary Examiner* — Hoa (Holly) Le
(74) *Attorney, Agent, or Firm* — Pabst Patent Group LLP

(57) ABSTRACT

Embodiments of the present disclosure provide for conjugated polymer nanoparticle, method of making conjugated polymer nanoparticles, method of using conjugated polymer nanoparticle, polymers, and the like.

20 Claims, 3 Drawing Sheets

(51) Int. Cl.
    C09K 11/06    (2006.01)
    C08J 3/12     (2006.01)
    C08J 3/07     (2006.01)
    A61K 49/00    (2006.01)
    C07D 417/14   (2006.01)
    G01N 33/58    (2006.01)
(52) U.S. Cl.
    CPC .  C08G 2261/124 (2013.01); C08G 2261/149 (2013.01); C08G 2261/1412 (2013.01); C08G 2261/18 (2013.01); C08G 2261/226 (2013.01); C08G 2261/228 (2013.01); C08G 2261/314 (2013.01); C08G 2261/3223 (2013.01); C08G 2261/3241 (2013.01); C08G 2261/3243 (2013.01); C08G 2261/3246 (2013.01); C08G 2261/3328 (2013.01); C08G 2261/344 (2013.01); C08G 2261/354 (2013.01); C08G 2261/364 (2013.01); C08G 2261/522 (2013.01); C08G 2261/90 (2013.01); C08G 2261/94 (2013.01); C08J 2365/00 (2013.01); C09K 2211/1483 (2013.01)

(56) References Cited

OTHER PUBLICATIONS

Chang et al, Electrogenerated Chemiluminescence of Single Conjugated Polymer Nanoparticles, J. Am. Chem. Soc. 2008, 130, 8906-8907 (Year: 2008).*

Du, C., et al., "Ethynylene-Containing Donor-Acceptor Alternating Conjugated Polymers: Synthesis and Photovoltaic Properties," Journal of Polymer Science, Polymer Chemistry, Jan. 15, 2013, vol. 51, pp. 383-393.

Feng, L., et al., "Conjugated Polymer Nanoparticles: Preparation, Properties, Functionalization and Biological Application," Chemical Society Reviews, Jun. 7, 2013, vol. 42, pp. 6620-6633.

Fujita, H., et al., "Synthesis and Photovoltaic Properties of 1,8-Carbazole-Based Donor-Acceptor Type Conjugated Polymers," Macromolecular Chemistry and Physics, Feb. 27, 2012, vol. 213, No. 4, pp. 447-457.

International Search Report in related International Application No. PCT/IB2016/055330, dated Oct. 27, 2016.

Liu, P., et al., "Red-Emitting DPSB-Based Conjugated Polymer Nanoparticles with High Two-Photon Brightness for Cell Membrane Imaging," Applied Materials & Interfaces, Apr. 1, 2015, vol. 7, No. 12, pp. 6754-6763.

Michinobu, T., et al., "Multicolor Emission and Thin Film Transistor Properties of 1,8-Diethynylcarbazole-Based Conjugated Copolymers," Polymer, Nov. 28, 2011, vol. 52, pp. 5756-5763, Elsevier Science Publishers B.V., GB.

Pecher, J., et al., "Nanoparticles of Conjugated Polymers," Chemical Reviews, Oct. 13, 2010, vol. 110, No. 10, pp. 6260-6279.

Robin, M.P., et al., "Strategies for Preparing Fluorescently Labelled Polymer Nanoparticles," Polymer International, Nov. 13, 2014, vol. 64, No. 2, pp. 174-182.

Written Opinion of the International Searching Authority in related International Application No. PCT/IB2016/055330, dated Oct. 27, 2016.

Li, S., et al., "Conjugated-Polymer-Based Red-Emitting Nanoparticles for Two-Photon Excitation Cell Imaging with High Contrast," Langmuir, Jun. 24, 2014, vol. 30, pp. 7623-7627.

Liu, J., et al., "Far-Red/Near-Infrared Conjugated Polymer Nanoparticles for Long-Term In Situ Monitoring of Liver Tumor Growth," Advanced Science, Apr. 20, 2015, vol. 2, pp. 1-7.

Lui, J., et al., "Bright Far-Red/Near-Infrared Fluorescent Conjugated Polymer Nanoparticles for Targeted Imaging of HER2-Positive Cancer Cells," Polymer Chemistry, May 29, 2013, vol. 4, pp. 4326-4334.

Winnard, Jr., P.T., et al., "Noninvasive Optical Tracking of Red Fluorescent Protein-Expressing Cancer Cells in a Model of Metastatic Breast Cancer," Neoplasia, Oct. 2006, vol. 8, No. 10, pp. 796-806.

* cited by examiner

CONJUGATED POLYMER NANOPARTICLES, METHODS OF USING, AND METHODS OF MAKING

CROSS-REFERENCE TO RELATED APPLICATIONS

This application is a U.S. National Stage of International Application No. PCT/IB2016/055330, which claims the benefit of and priority to U.S. Provisional Application Ser. No. 62/216,584, having the title "CONJUGATED POLYMER NANOPARTICLES, METHODS OF USING, AND METHODS OF MAKING," filed on Sep. 10, 2015, the disclosures of which are incorporated herein by reference in their entirety.

BACKGROUND

The development of probes for fluorescence imaging is an area that is currently attracting considerable attention across a wide range of fields. Fluorescent probes are one of the cornerstones in the interdisciplinary fields of materials chemistry, biology and medicine. The understanding of complex systems is increasingly dependent on the ability to visualize and quantify signaling molecules with high spatial and temporal resolution. Great efforts have been made toward the development of new probes with high fluorescence efficiency in the red spectral region. So far, various materials including fluorescent proteins, small organic fluorophores, dye-doped beads or inorganic semiconductor quantum dots have been widely exploited for fluorescence imaging. However, the use of organic fluorophores and fluorescent proteins is hampered by inherent drawbacks such as poor photostability and blinking behavior. Dye-doped beads have a relatively large size and limited protection of the dye molecules, making these probes prone to leaching. Quantum dots show greater fluorescent quantum yields and greater tolerance to photobleaching compared to organic dyes. However, QDs are hydrophobic by nature, thereby they require layers of polymeric or inorganic material to make them compatible them with the aqueous environment. Moreover in the oxidative environment they tend to leak metal ions, inducing cytotoxicity. Thus, there is a need to overcome these deficiencies or difficulties.

SUMMARY

Embodiments of the present disclosure provide for conjugated polymer nanoparticle, method of making conjugated polymer nanoparticles, method of using conjugated polymer nanoparticle, polymers, and the like.

An embodiment of the present disclosure includes a conjugated polymer nanoparticle comprising a polymer including the following structure:

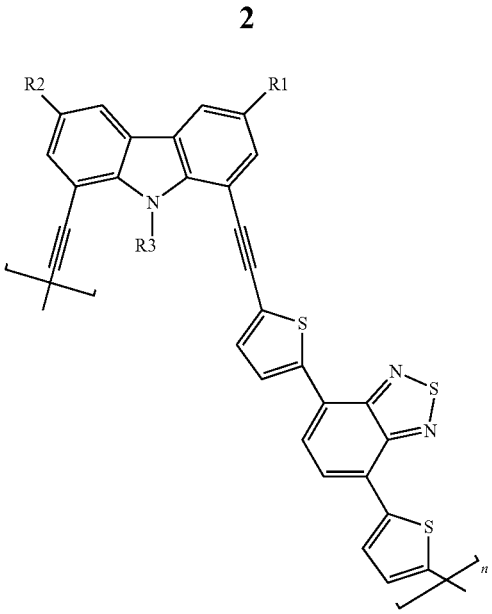

wherein R1 is H or an aliphatic group, R2 is H or an aliphatic group, R3 is H or an aliphatic group, and n is 1 to 10,000. In an embodiment, each aliphatic group is independently selected from the group consisting of: a saturated or unsaturated, linear or branched, alkyl group, a cycloalkyl group, an aryl group, a heteroaryl group, and a heterocyclic group, wherein each group is independently substituted or unsubstituted. In an embodiment, each aliphatic group is independently selected from the group consisting of: $C_4H_9$, $C_8H_{17}$, and $C_{16}H_{33}$. In an embodiment, only two of the aliphatic groups are identical and in another embodiment, each of the aliphatic groups are different.

In an embodiment, polymer includes the following structure:

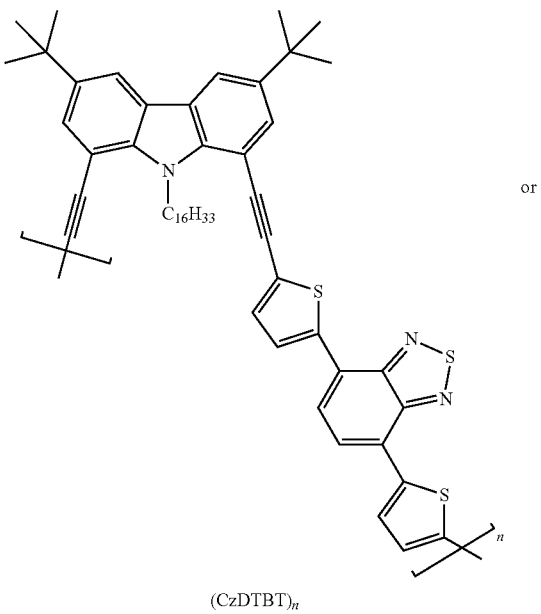

(CzDTBT)$_n$

-continued

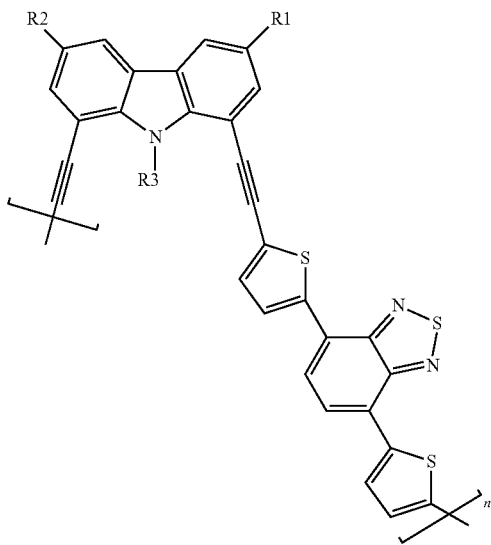

[(CzDTBT)$_n$]-2

An embodiment of the present disclosure includes a compound comprising the following structure:

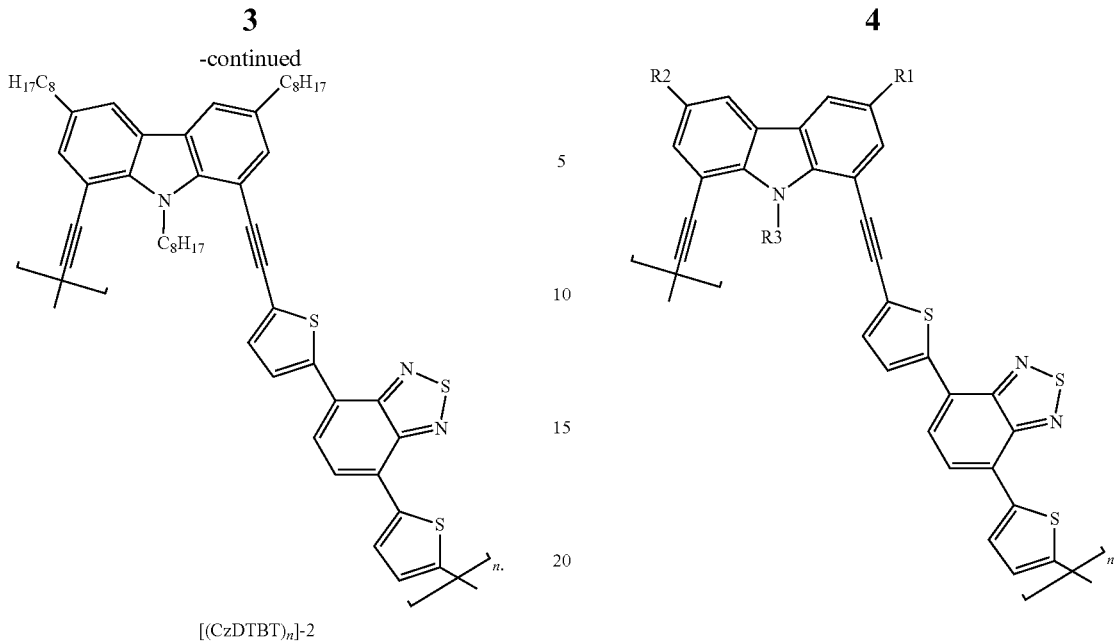

wherein R1 is H or an aliphatic group, R2 is H or an aliphatic group, R3 is H or an aliphatic group, and n is 1 to 10,000.

An embodiment of the present disclosure includes a method of making conjugated polymer nanoparticles, comprising: sonicating a solution including a polymer and a solvent for a time period of about 45 to 75 minutes at a temperature of about 2° C.-6° C.; flowing a gas through the solution to remove the solvent; and forming the conjugated polymer nanoparticles, wherein the polymer has the following structure:

wherein R1 is H or an aliphatic group, R2 is H or an aliphatic group, R3 is H or an aliphatic group, and n is 1 to 10,000.

Other compositions, methods, features, and advantages will be or become apparent to one with skill in the art upon examination of the following drawings and detailed description. It is intended that all such additional compositions, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1A:
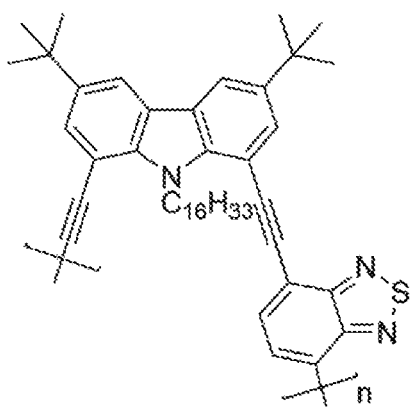
FIGS. 1A-B are chemical structures of (FIG. 1A) (CzBT)$_n$ and (FIG. 1B) (CzDTBT)$_n$.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, inorganic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced (e.g., halogen, small alkyl group, and the like), provided that the designated atom's normal valence is not exceeded.

As used herein, "aliphatic" or "aliphatic group" refers to a saturated or unsaturated, linear or branched, cyclic (aromatic or non-aromatic) or heterocyclic (aromatic or non-aromatic), hydrocarbon or hydrocarbon group and encompasses alkyl, alkenyl, and alkynyl groups, and alkanes, alkene, and alkynes, for example, where the aliphatic group (e.g., R1, R2, and/or R3) can bound through a single bond as indicated in the structures herein. In an embodiment, the aliphatic group can have about 1 to 30 carbons, about 2 to 20 carbons, or about 4 to 16 carbons. In an embodiment, the aliphatic group can be substituted or unsubstituted.

As used herein, "cyclic" group refers to a cyclic hydrocarbon (substituted or unsubstituted) having a stable 4, 5, 6, 7, 8, 9, 10, 11, or 12 membered (e.g., carbon or hetero), (unless the number of members is otherwise recited), monocyclic, bicyclic, or tricyclic cyclic ring. As used herein, "heterocyclic" group refers to a heterocyclic hydrocarbon (substituted or unsubstituted) having a stable 4, 5, 6, 7, 8, 9, 10, 11, or 12 membered ring structure (substituted or unsubstituted) where one of the carbon atoms is substituted with one or more non-carbon atoms, such as oxygen, nitrogen, and sulfur, in the ring.

As used herein, "alkyl" or "alkyl group" refers to a saturated aliphatic hydrocarbon radical (substituted or unsubstituted) which can be straight or branched, having about 1 to 30 carbon atoms, about 2 to 20 carbon atoms, or about 4 to 16 carbon atoms, wherein the stated range of carbon atoms includes each intervening integer individually, as well as sub-ranges. Examples of alkyl include, but are not limited to methyl, ethyl, n-propyl, i-propyl, n-butyl, sec-butyl, t-butyl, n-pentyl, isopentyl and sec-pentyl. The term "lower alkyl" means an alkyl group having less than 10 carbon atoms.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(alkyl), —N(alkyl)$_2$, alkoxy, alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system (substituted or unsubstituted) of about 4 to 30 carbon atoms, about 6 to 20 carbon atoms, or about 6 to 16 carbon atoms. Exemplary aryl groups include phenyl or naphthyl, or substituted phenyl or substituted naphthyl.

The term "heteroaryl" is used herein to denote an aromatic ring or fused ring structure (substituted or unsubstituted) of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

General Discussion

Embodiments of the present disclosure provide for conjugated polymer nanoparticles, methods of making conjugated polymer nanoparticles, methods of using conjugated polymer nanoparticles, polymers, and the like. In general conjugated polymer nanoparticle can be used in fluorescence imaging, drug/gene deliver, anticancer and anti-microorganism activity, targeted in vitro/in vivo cellular imaging, intracellular biomolecule imaging, and in vivo small molecule imaging. The optical properties of the conjugated polymer nanoparticle can be tailored to the requirements of a particular use. The conjugated polymer nanoparticle of the present disclosure can be advantageous to use due to their high brightness, good photostability, and low cytotoxicity.

In an embodiment, conjugated polymer nanoparticles are attractive for sensing and labeling target cells or tissues in biological applications. In embodiment, the conjugated polymer nanoparticle can be labeled with an agent, which can be used to enable, assist, enhance, improve, or the like use of the conjugated polymer nanoparticle image, detect, study, monitor, evaluate, and the like, a disease, condition, a biological system, a cell, a tissue, an organ, or the like.

Exemplary embodiments of the present disclosure are directed to a conjugated polymer nanoparticle that includes a polymer. In an embodiment, the conjugated polymer nanoparticle can have a spherical or semi-spherical shape. In an embodiment, the conjugated polymer nanoparticle has a longest dimension (e.g., diameter for a spherical type of particle) of about 2 to 8 nm or about 3 to 6 nm.

In an embodiment, the nanoparticle can have a zeta potential that can be advantageous. The value of the zeta potential reflects the effective charge on the surface of the nanoparticle and is related to the electrostatic repulsion among particles, as a result, the zeta potential can be used to determine colloidal stability of suspension. In an embodiment, the nanoparticles showed good stability over a 6 month time frame, confirming the zeta potential results. In an embodiment, the nanoparticle can have a zeta potential of about 52-56 mV or about 54 mV.

In an embodiment, the nanoparticle can have an absorption maximum at about 505 nm. In an embodiment, the nanoparticle can have a photoluminescence with an emission peak at about 660 nm. In an embodiment, the nanoparticle can have a fluorescence quantum yield of about 20% using Rhodamine 101 and Rhodamine 6G in ethanol as references.

In an embodiment, the polymer includes following structure:

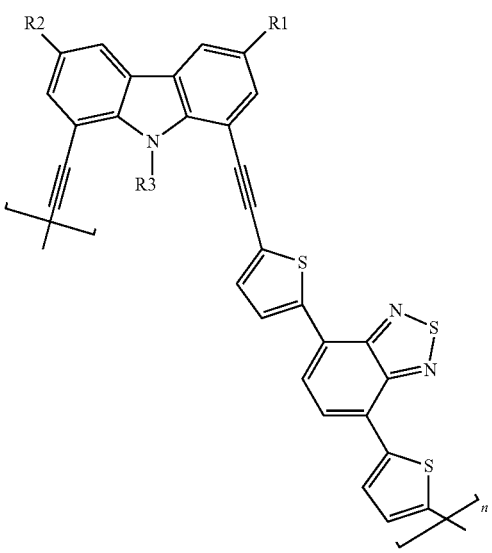

where R1 can be H or an aliphatic group, R2 can be H or an aliphatic group, R3 can be H or an aliphatic group, and n is 1 to 10,000, about 1 to 1000, about 1 to 100, or about 1 to 10. In an embodiment, R1, R2, and R3 are the same, two of R1, R2, and R3 are the same, or each of R1, R2, and R3 are different.

In an embodiment, the aliphatic group can include a saturated or unsaturated, linear or branched, cyclic (aromatic or non-aromatic) or heterocyclic (aromatic or non-aromatic), hydrocarbon group. In an embodiment, the aliphatic group can be substituted or unsubstituted. In an embodiment, each aliphatic group can be independently be: a saturated or unsaturated, linear or branched, alkyl group, a cycloalkyl group, an aryl group, a heteroaryl group, and a heterocyclic group. In an embodiment, the aliphatic group can have about 1 to 30 carbon atoms, about 2 to 20 carbon atoms, or about 4 to 16 carbon atoms. For example, the aliphatic group can include an alkyl group or a cyclic group including an aryl group having a stable 4, 5, 6, 7, 8, 9, 10, 11, or 12 membered (e.g., carbon or hetero), (unless the number of members is otherwise recited), monocyclic, bicyclic, or tricyclic cyclic ring. In an embodiment, the polymer can be a copolymer with two or more units where the R groups in each are not identical. In an embodiment, each aliphatic group can be independently selected from: $C_4H_9$, $C_8H_{17}$, and $C_{16}H_{33}$.

In an embodiment, the polymer can include the following structures:

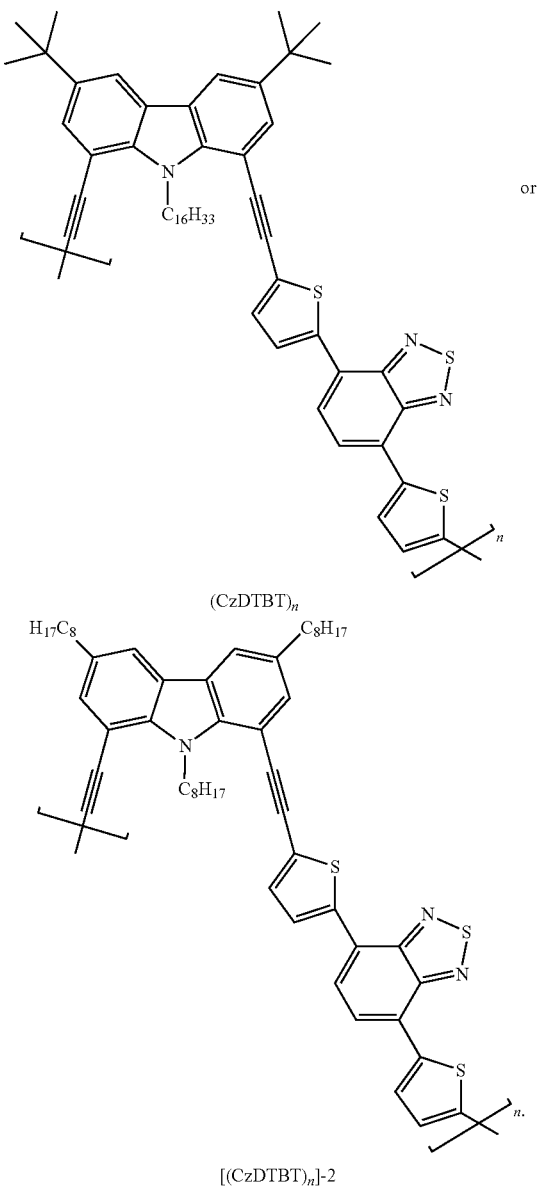

(CzDTBT)$_n$

[(CzDTBT)$_n$]-2

In an embodiment, the conjugated polymer nanoparticle can include one or more agents (e.g., a chemical or biological agent), where the agent can be disposed indirectly or directly on the conjugated polymer nanoparticle. In an embodiment, the agent can include, but is not limited to, a drug, a therapeutic agent, a radiological agent, a small molecule drug, a biological agent (e.g., polypeptides (e.g., proteins such as, but not limited to, antibodies (monoclonal or polyclonal)), antigens, nucleic acids (both monomeric and oligomeric), polysaccharides, haptens, sugars, fatty acids, steroids, purines, pyrimidines, ligands, and aptamers), a cell, and combinations thereof, that can be used to image, detect, study, monitor, evaluate, and the like. In an embodiment, the agent is included in an effective amount to accomplish its purpose, where such factors to accomplish the purpose are well known in the medical arts.

In general, the agent can be bound to the conjugated polymer nanoparticle by a physical, biological, biochemical, and/or chemical association directly or indirectly by a suitable means. The term "bound" can include, but is not limited to, chemically bonded (e.g., covalently or ionically), biologically bonded, biochemically bonded, and/or otherwise associated with the conjugated polymer nanoparticle. In an embodiment, being bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, π-π stacking interactions, combinations thereof, and like interactions.

In an embodiment, a method of making conjugated polymer nanoparticles can include sonicating a solution including a polymer and a solvent. The polymer includes the polymer described herein. In an embodiment, the solvent can be tetrahydrofuran (THF), for example. The solution can be sonicated at a frequency of about 30 to 45 kH or about 37 kH and an effective power of about 150 to 210 W or about 180 W for a time period of about 45 minutes to 75 minutes or about one hour at a bath temperature of about 0 to 10° C., about 2 to 6° C., or about 4° C. In an embodiment, a gas or gas mixture can be flowed (e.g., bubbled) through the solution to remove the solvent and/or and subsequently concentrate the polymer nanoparticle suspension. In an embodiment the gas can be flowed during and/or after sonication. In an embodiment, the gas can be dried air, an inert gas (e.g., argon, nitrogen), a noble gas, a gas that can remove the solvent, or a combination thereof and the bath temperature can be about 30 to 40° C. for a time frame appropriate to reach the desired concentration of the polymer nanoparticles. After sonication and gas flow, a suspension including the conjugated polymer nanoparticles is produced. Additional details are provided in Example 1.

As mentioned above, the present disclosure relates generally to methods for studying (e.g., detecting, localizing, or quantifying) biological related events or analysis such as fluorescence imaging, drug/gene deliver, anticancer and anti-microorganism activity, targeted in vitro/in vivo cellular imaging, intracellular biomolecule imaging, in vivo small molecule imaging cellular events, in vivo cell trafficking, stem cell studies, tumor imaging, biomolecule array systems, biosensing, biolabeling, gene expression studies, protein studies, medical diagnostics, diagnostic libraries, microfluidic systems, and delivery vehicles. The present disclosure also relates to methods for imaging of event(s) substantially simultaneously inside a subject (e.g., a host living cell, tissue, or organ, or a host living organism) using embodiments of the present disclosure.

In short, the conjugated polymer nanoparticle is introduced to the subject using known techniques. The conjugated polymer nanoparticles can also be labeled with one or more types of agents for the particular study (e.g., agents targeted to or directed to cancer imaging and/or treatment), as mentioned above.

At an appropriate time, the conjugated polymer nanoparticles and/or agent can be detected and quantified using a detection system, as known in the art. The measured signal is or can be correlated to the feature being studied. In an embodiment, the detection of the conjugated polymer nanoparticles and/or agent can be conducted after a sufficient time frame to allow unassociated conjugated polymer nanoparticles to be sufficiently cleared from the appropriate area, region, or tissue of interest.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Figure 1B:
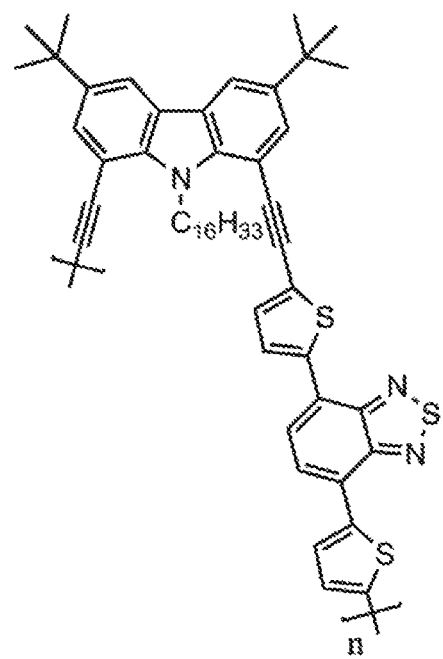

Herein, we present a new red fluorescent conjugated polymer particles based on a series of donor-acceptor-type poly(1,8-carbazole)-benzothiadiazole ((CzBT)$_n$) copolymer and poly(1,8-carbazole)-dithienylbenzothiadiazole ((CzDTBT)$_n$) copolymer molecules (FIGS. 1A-B). The particles were prepared using a modified reprecipitation method. The size and morphology of particles were studied by transmission electron microscopy (TEM) which revealed fairly spherical shape with a size range of 3-6 nm. Our extremely small polymer dots possess a high fluorescence quantum efficiency reaching of $\Phi_{Fl}$=0.2 and strong photobleaching resistance ($\Phi_{bl}$=7.25±10-12).

Conjugated polymer nanoparticles with emission spanning the full range of the visible spectrum have been developed by fine tuning of the conjugated structures e.g. employing copolymerization or varying linkage bonds. Red emitting conjugated polymers generally have planar aromatic structures, which make them easy to aggregate in aqueous environment via π-π stacking and hydrophobic interaction, leading to significantly reduced photoluminescence quantum efficiency. In general, the quantum efficiency decreases sharply with changing the emission from blue to red. Quantum yields of the most reported red luminescent polymer nanoparticles are below 2% because of aggregation induced quenching. Our previous study on single (CzBT)$_n$ molecules (n=1 to 10,000 and as defined herein) embedded in a hydrophobic polymer, Zeonex film, strongly suggest that the polymer molecules adopt different twist structures which can reduce π-π stacking effect. Separating adjacent conjugated segments helps to mitigate the self-quenching effects and leads to higher quantum yields. In two reported cases of polymer particles with high photoluminescence quantum efficiency in red spectral region, the size of formed nanoparticles exceeds 20 nm and 150 nm respectively (Liu, P. et al., ACS Appl. Mater. Interfaces, 2015, 7, 6754; Lju, J. et al., Adv. Sci. 2015, 2, 1500008). Preparation of nanoparticles by the reprecipitation method generally yielded primary particles in the size range of several tens of nanometers. In very rare case, particle sizes less than 10 nm have been obtained by the method (Pecher, J, Mecking, S. Chemical Reviews, 2010, 110, 6260).

In the present example, conjugated polymer based nanoparticles were prepared through modified nanoprecipitation method at low temperature 4° C. which is followed by self-assembly of polymer chains sustaining their high fluorescence quantum yield and stability in water medium. Briefly, 2 ml solution of well dissolved polymer in THF (containing polymer in concentration 5 μg/ml) was added into 6 ml of Milli-Q water under 1 hour continuous sonication. The sonication under the low temperature (i.e., 4° C.) lead to particles with highest fluorescence quantum efficiency. Further, the continuous flow of compressed dry air was used to remove remaining THF and concentrate obtained particle suspension. Previously reported preparation methods were based on short sonication times followed by heating of obtained mixture on hot magnetic plate above 60° C. to evaporate the organic solvent. In the case of our polymers, this approach was leading to turbid suspension of polymer aggregates. In our modified preparation procedure, we extended the sonication process and followed it by continuous air flow to remove remaining organic solvent. Additionally, we found that low temperature (i.e., 4° C.) preparation leads to brighter polymer nanoparticles (i.e., high quantum yields). The long-lasting sonication at low temperature allows for more stable nanoparticle formation process e.g., by protecting the mixture from dynamic changes in organic phase concentration due to the evaporation at elevated temperatures.

Figure 2:
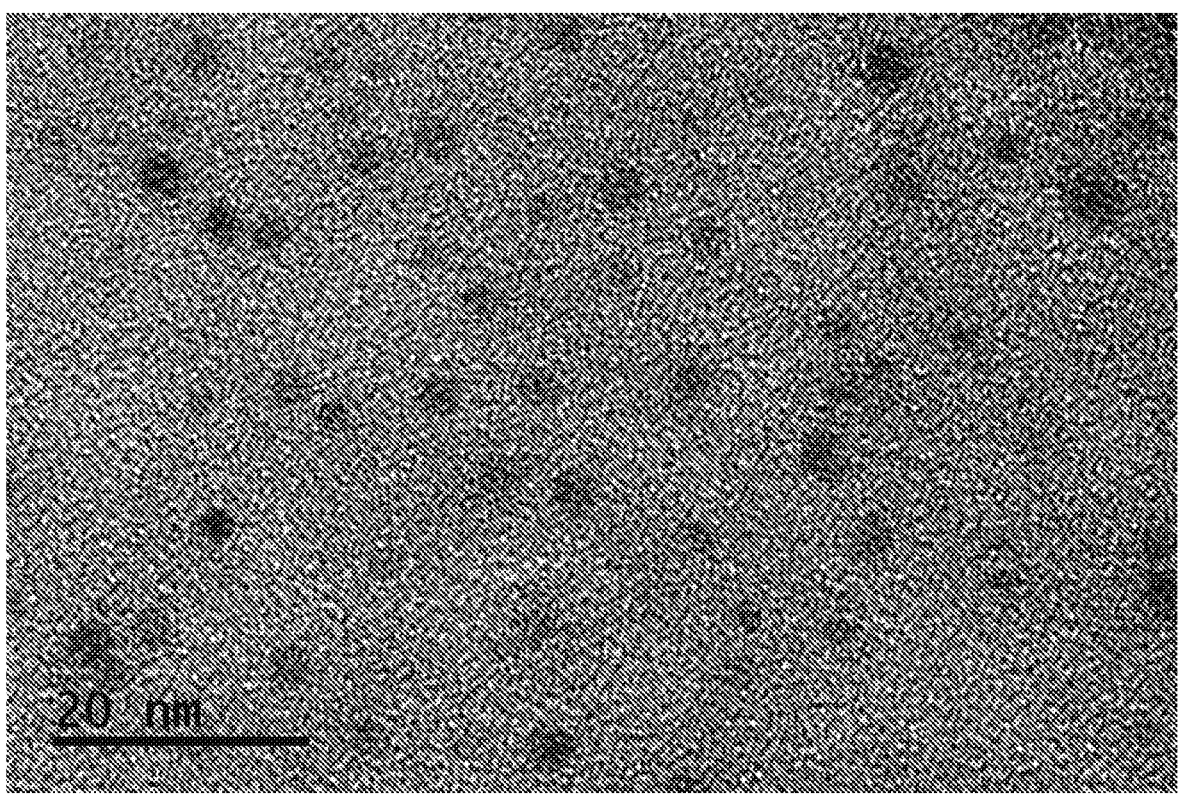
FIG. 2 is a TEM analysis demonstrating that the (CzBT)$_n$ nanoparticles exhibited a diameter in the range of 3-5 nm.

The measured zeta potential of the nanoparticles aqueous suspension was 51 [mV] and 54 [mV] for (CzBT)$_n$ and (CzDTBT)$_n$, (n=1 to 10,000 and as defined herein) respectively. The value of zeta potential reflects the effective charge on the particle surface and is therefore related to the electrostatic repulsion among particles, which provide good colloidal stability of suspensions. The obtained nanoparticles were kept in a refrigerator. After 6 month, the nanoparticles suspension does not show any obvious change, confirming that the nanoparticles have good colloidal stability. The size and morphology of the nanoparticles were studied by transmission electron microscopy (TEM). TEM samples were scanned with a FEI Tecnai™ microscope operated at 120 kV. Samples were prepared by dropcasting on copper grids followed by drying at room temperature. The nanoparticles have spherical shape with a typical diameter in the range of 3-5 nm (see FIG. 2).

Figure 3:
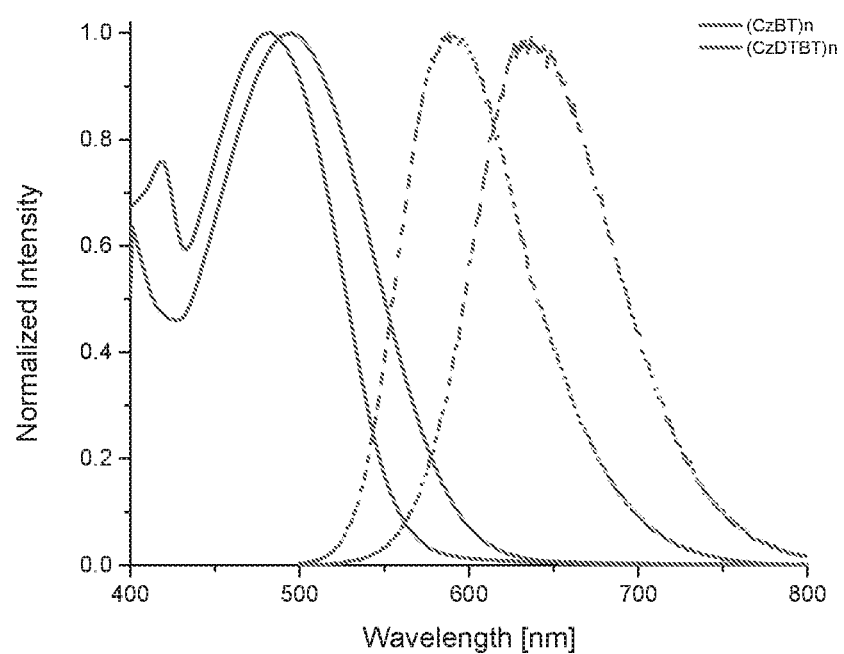
FIG. 3 shows the absorption and photoluminescence spectra of polymer (CzBT)$_n$ and (CzDTBT)$_n$ nanoparticles in water. Our particles have an absorption peak between 498 and 505 nm with an emission maximum at 630-660 nm, which gives rise to a remarkably large Stoke shifts of up to 150 nm.

FIG. 3 shows UV-Vis and fluorescence spectra of (CzBT)$_n$ and (CzDTBT)$_n$ nanoparticles in water. The absorption of (CzBT)$_n$ and (CzDTBT)$_n$ have absorption peak maximum centered at 498 nm and 505 nm, respectively. Polymer nanoparticles exhibit a photoluminescence spectrum with an emission peak at 630 for (CzBT)$_n$ and 660 for (CzDTBT)$_n$. The fluorescence quantum yield ($\Phi_{fl}$) of nanoparticles was measured to be 16±2% for (CzBT)$_n$ and 20±2% for (CzDTBT)$_n$ using Rhodamine 101 ($\Phi_{fl}$=96%) and Rhodamine 6G ($\Phi_{fl}$=94%) in ethanol as references.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A composition comprising conjugated polymer nanoparticles with a diameter in the range of 2-5 nm as measured by Transmission Electron Microscopy (TEM), the nanoparticles comprising a polymer including the following structure:

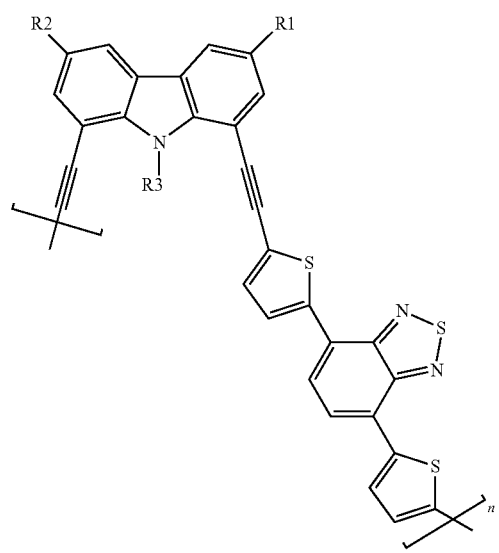

wherein R1 is H or an aliphatic group, R2 is H or an aliphatic group, R3 is H or an aliphatic group, and n is an integer between 1 and 10,000.

2. The composition of claim 1, wherein each aliphatic group is independently selected from the group consisting of: a saturated or unsaturated, linear or branched, alkyl group, a cycloalkyl group, an aryl group, a heteroaryl group, and a heterocyclic group, wherein each group is independently substituted or unsubstituted.

3. The composition of claim 2, wherein each aliphatic group is independently selected from the group consisting of: $C_4H_9$, $C_8H_{17}$, and $C_{16}H_{33}$.

4. The composition of claim 1, wherein only two of the aliphatic groups are identical.

5. The composition of claim 1, wherein each aliphatic group is different.

6. The composition of claim 1, wherein the polymer includes the following structure:

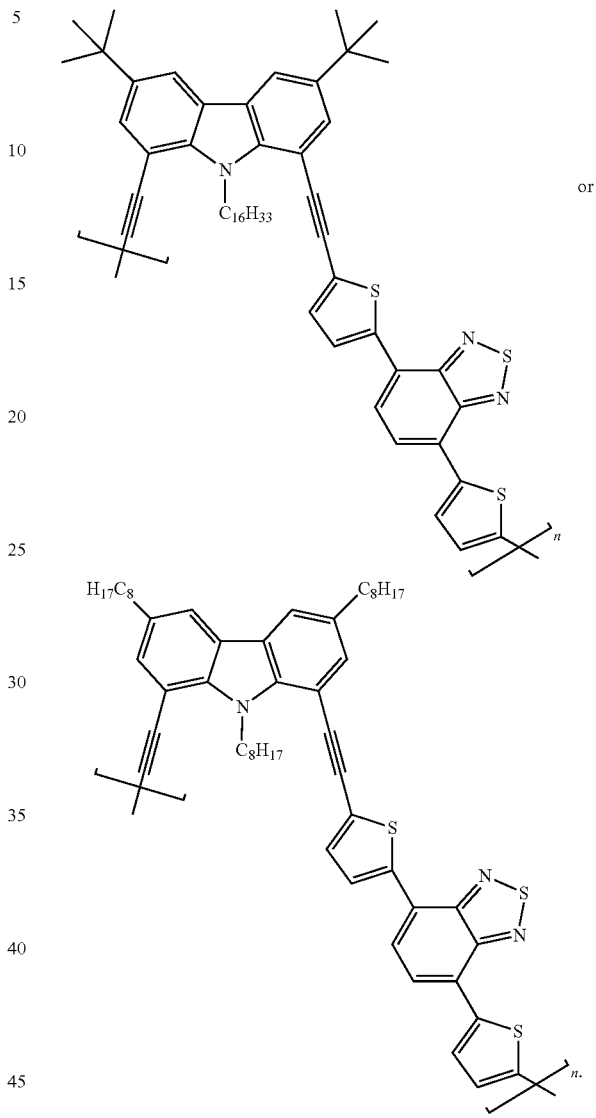

7. The composition of claim 6, wherein the nanoparticle has a diameter of about 3 nm, as measured by TEM.

8. The composition of claim 1, wherein the nanoparticle has a zeta potential of about 52-56 mV in aqueous suspension.

9. The composition of claim 1, wherein the nanoparticle has an absorption maximum at about 505 nm in water.

10. The composition of claim 1, wherein the nanoparticle has a photoluminescence with an emission peak at about 660 nm in water.

11. The composition of claim 1, wherein the nanoparticle has a fluorescence quantum yield of about 20% in water using Rhodamine 101 and Rhodamine 6G in ethanol as references.

12. The composition of claim 1, wherein one or more of the aliphatic groups have about 1 to 30 carbons, about 2 to 20 carbons, or about 4 to 18 carbons.

13. A method of making conjugated polymer nanoparticles, comprising:
sonicating a solution including a polymer and a solvent for a time period of about 45 to 75 minutes at a temperature of about 0-10° C.;
flowing a gas through the solution to remove the solvent; and
forming the conjugated polymer nanoparticles,
wherein the polymer has the following structure:

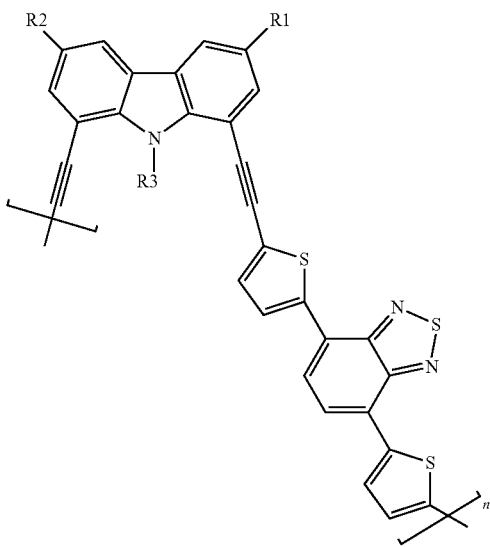

wherein R1 is H or an aliphatic group, R2 is H or an aliphatic group, R3 is H or an aliphatic group, and n is an integer between 1 and 10,000.

14. The method of claim 13, wherein the solvent is THF.

15. The method of claim 13, wherein the gas is selected from the group consisting of: air, a purified gas, and a combination thereof.

16. The method of claim 13 wherein each aliphatic group is independently selected from the group consisting of: a saturated or unsaturated, linear or branched, alkyl group, a cycloalkyl group, an aryl group, a heteroaryl group, and a heterocyclic group, wherein each group is independently substituted or unsubstituted.

17. The method of claim 16, wherein each aliphatic group is independently selected from the group consisting of: $C_4H_9$, $C_8H_{17}$, and $C_{16}H_{33}$.

18. The method of claim 13, wherein the temperature of sonicating is about 2-6° C. or about 4° C.

19. The method of claim 13, wherein one or more of the aliphatic groups have about 1 to 30 carbons, about 2 to 20 carbons, or about 4 to 18 carbons.

20. A conjugated polymer nanoparticle composition prepared according to the method of claim 13, wherein the composition comprises nanoparticles with a diameter in the range of 2-5 nm as measured by Transmission Electron Microscopy (TEM).

* * * * *